US012559456B2

(12) United States Patent
Hu

(10) Patent No.: US 12,559,456 B2
(45) Date of Patent: Feb. 24, 2026

(54) METHOD FOR PREPARING LEVETIRACETAM AND INTERMEDIATES THEREOF

(71) Applicant: Suzhou BrightHope Pharmatech Co., Ltd, Jiangsu Province (CN)

(72) Inventor: Songzhou Hu, Princeton, NJ (US)

(73) Assignee: SUZHOU BRIGHTHOPE PHARMA TECH CO., LTD, Jiangsu Province (CN)

( * ) Notice: Subject to any disclaimer, the term of this patent is extended or adjusted under 35 U.S.C. 154(b) by 917 days.

(21) Appl. No.: 17/847,898

(22) Filed: Jun. 23, 2022

(65) Prior Publication Data

US 2022/0324801 A1 Oct. 13, 2022

Related U.S. Application Data

(63) Continuation-in-part of application No. 17/166,662, filed on Feb. 3, 2021, now Pat. No. 11,384,050.

(51) Int. Cl.
*C07D 207/267* (2006.01)

(52) U.S. Cl.
CPC ................................ *C07D 207/267* (2013.01)

(58) Field of Classification Search
CPC ................................................. C07D 207/267
See application file for complete search history.

(56) References Cited

U.S. PATENT DOCUMENTS

| | | | | |
|---|---|---|---|---|
| 4,696,942 | A | 9/1987 | Gobert et al. | |
| 4,696,943 | A | 9/1987 | Gobert et al. | |
| 4,837,223 | A | 6/1989 | Gobert et al. | |
| 4,943,639 | A | 7/1990 | Gobert et al. | |
| 6,107,492 | A | 8/2000 | Futagawa et al. | |
| 6,124,473 | A | 9/2000 | Cavoy et al. | |
| 6,686,477 | B2 | 2/2004 | Boaz et al. | |
| 6,713,635 | B2 | 3/2004 | Surtees et al. | |
| 7,122,682 | B2 | 10/2006 | Ates et al. | |
| 7,132,552 | B2 * | 11/2006 | Dolitzky | C07D 207/27 548/543 |
| 7,291,746 | B2 * | 11/2007 | Surroca | A61K 31/4015 548/518 |
| 7,563,912 | B2 | 7/2009 | Ates et al. | |
| 7,902,380 | B2 | 3/2011 | Li et al. | |
| 7,939,676 | B2 | 5/2011 | Colli et al. | |
| 8,492,416 | B2 | 7/2013 | Kenda et al. | |
| 11,384,050 | B1 * | 7/2022 | Hu | C07C 253/30 |

FOREIGN PATENT DOCUMENTS

| | | | |
|---|---|---|---|
| CN | 101333180 | B | 5/2011 |
| CN | 104844485 | B | 1/2017 |
| CN | 108409592 | A | 8/2018 |
| CN | 110590635 | A | 12/2019 |
| GB | 1309692 | | 3/1973 |
| WO | 2005/42516 | A2 | 5/2005 |
| WO | 2019028666 | A1 | 2/2019 |
| WO | 2019028669 | A1 | 2/2019 |
| WO | 2020216146 | A1 | 10/2020 |

OTHER PUBLICATIONS

International Search Report and Written Opinion issued for International Patent Application No. PCT/US2022/014698, mailed May 12, 2022.

Boschi, Francesca et al., "A synthesis of levetiracetam based on (S)-N-phenylpantolactam as a chiral auxiliary", Science Direct, Nov. 2005, pp. 3739-3745, vol. 16, No. 22, Elsevier.

Non-Final Office Action issued for U.S. Appl. No. 17/166,662 electronically delivered on Jan. 27, 2022.

American Chemistry Society (ACS), CAS Registry, CAS Registry No. 1248421-42-2, Chemical Catalog, Ukrorgsyntez, Ltd., Oct. 29, 2010.

* cited by examiner

*Primary Examiner* — Golam M Shameem
(74) *Attorney, Agent, or Firm* — Myers Wolin, LLC

(57) ABSTRACT

There is disclosed a method for preparing levetiracetam and intermediates from a compound of the formula:

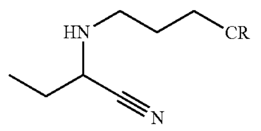

wherein CR is selected from the group consisting of cyano, carboxylic acid, carboxamide, alkali carboxylate, alkaline earth metal carboxylate, alkyl carboxylate, and a mixture thereof.

3 Claims, No Drawings

METHOD FOR PREPARING LEVETIRACETAM AND INTERMEDIATES THEREOF

CROSS REFERENCE TO RELATED APPLICATIONS

This application is a continuation-in-part of U.S. application Ser. No. 17/166,662, filed on Feb. 3, 2021, which is incorporated herein by reference.

FIELD OF THE INVENTION

This invention relates to N-(3-substituted propyl)-2-aminobutyronitrile, its preparation, and its use for preparing levetiracetam and intermediates thereof.

BACKGROUND OF THE INVENTION

Levetiracetam is the S-enantiomer of etiracetam in a class of medications called anticonvulsants. It is used in combination with other medications to treat certain type of seizures in adults and children with epilepsy. Levetiracetam has the following structure:

(I)

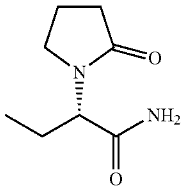

Although numerous methods have been developed for preparing levetiracetam, it is commercially produced by one of the two methods first disclosed in GB 1309692 and U.S. Pat. No. 4,696,943. In the first method, 2-pyrrolidinone and alkyl 2-halobutyrate are used as the starting materials in a process according to the following reaction scheme:

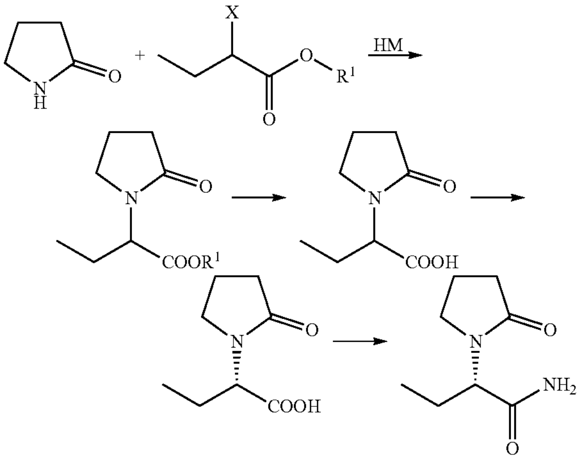

(I)

wherein X is halogen, HM is metal hydride, and $R^1$ is an alkyl group.

In the second method, L-2-aminobutanamide hydrochloride and alkyl 4-halobutyrate or 4-halobutyryl halide are used as the starting materials in a process according to the following reaction scheme:

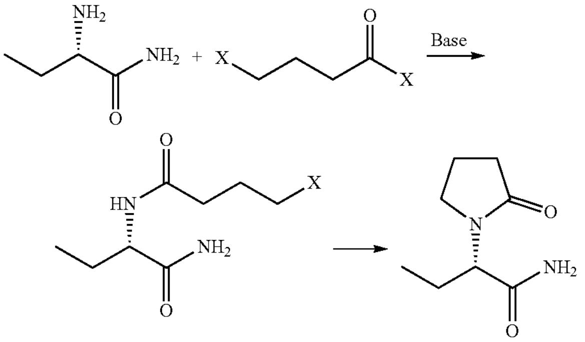

(I)

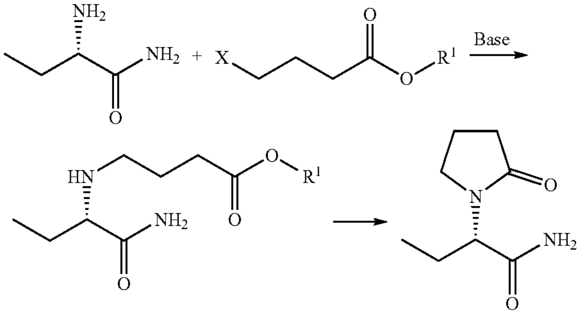

(I)

wherein X is halogen, $R^1$ is an alkyl group, and the base is an organic or inorganic base such as triethylamine or sodium carbonate.

There are inherent disadvantages in these two methods for the production of levetiracetam. In the process according to the first method, the metal hydride, which is required to deprotonate 2-pyrrolidinone, is dangerous to handle on a large scale and presents serious safety issues for the manufacturing plant. In addition, the alkyl 2-halobutyrate ester is not only unavailable commercially but also extremely obnoxious, posing environmental and occupational problems.

In the process according to the second method, just like the alkyl 2-halobutyate in the process of the first method, alkyl 4-halobutyrate and 4-halobutyryl halide are also extremely obnoxious, posing the same environmental and occupational problems. In addition, L-2-aminobutanamide hydrochloride is specifically produced for levetiracetam and as a result is costly. L-2-aminobutanamide hydrochloride is produced either from racemic 2-aminobutanamide by optical resolution or from L-2-aminobutyric acid, which is not one of the naturally occurring L-amino acids, but specifically produced for the purpose. Although there have been intensive efforts to improve the process for producing L-2-aminobutanamide hydrochloride and L-2-aminobutyric acid, they are still costly. In addition, during the cyclization under strongly basic condition, the product of levetiracetam is partially racemized or hydrolyzed. To obtain a product of pharmaceutical grade, extensive purification is required.

It is the object of the present invention to overcome these inherent disadvantages in the processes for preparing levetiracetam and to disclose a process for preparing levetiracetam and intermediates thereof from readily available starting materials. The process according to the present invention is concise, constructs all necessary structural elements in a one-pot synthesis, and reaches levetiracetam from commercially and economically available starting materials in far fewer steps than prior art processes.

SUMMARY OF THE INVENTION

This invention discloses novel intermediates of the following structural formula (II):

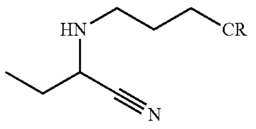

(II)

wherein CR is cyano, carboxylic acid, carboxamide, alkali carboxylate, alkaline earth metal carboxylate, alkyl carboxylate, and a mixture thereof, and wherein the alkali is lithium, sodium, potassium or a mixture thereof, wherein the alkaline earth metal is magnesium, calcium, barium, or a mixture thereof, and wherein the alkyl refers to $C_1$-$C_{12}$ of a straight, cyclic, or branched chain alkane radical containing from 1 to 12 carbon atoms, preferably the alkyl is $C_1$-$C_4$. These intermediates are useful for the preparation of levetiracetam.

The present invention also relates to processes for preparing the intermediates of formula (II), comprising the reaction of propionaldehyde, a source of cyanide, and a primary amine of formula $H_2NCH_2CH_2CH_2CR$, wherein CR is cyano, carboxylic acid, carboxamide, alkali carboxylate, alkyl carboxylate, and a mixture thereof; and wherein the source of cyanide is alkali cyanide, alkaline earth metal cyanide, zinc cyanide, or hydrogen cyanide. The alkali is lithium, sodium, potassium, or a mixture thereof. The alkaline earth metal is magnesium, calcium, barium, or a mixture thereof.

The present invention further relates to various methods for preparing levetiracetam and intermediates thereof from the novel intermediate of formula (II) by converting it to the key precursor of levetiracetam having the following structural formula:

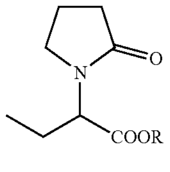

wherein R is hydrogen or a $C_1$-$C_{12}$ alkyl group.

DETAILED DESCRIPTION OF THE INVENTION

Definitions

The term "alkyl" refers to a straight, branched chain, or cyclic alkane (hydrocarbon) radical containing from 1 to 12 carbon atoms. Exemplary "alkyl" groups include methyl, ethyl, propyl, isopropyl, cyclopropyl, n-butyl, t-butyl, isobutyl, cyclobutyl, cyclopropylmethyl, pentyl, isopentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_8$ alkyl" refers to a straight, cyclic, or branched chain alkane radical containing from 1 to 8 carbon atoms, such as methyl, ethyl, propyl, isopropyl, cyclopropyl, n-butyl, t-butyl, isobutyl, cyclobutyl, cyclopropylmethyl, pentyl, isopentyl, hexyl, isohexyl, heptyl, 4,4-dimethylpentyl, and octyl.

The compounds of the present invention may form salts which are also within the scope of this invention. Reference to compounds of the formula (II) through (X) herein is understood to include reference to salts thereof, unless otherwise indicated. The term "salt(s)", as employed herein, denotes acidic and/or basic salts formed with inorganic and/or organic acids and bases.

The compounds of the present invention may form salts with a variety of organic and inorganic acids. Exemplary acid addition salts include hydrochloric acid, hydrobromic acid, sulfuric acid, nitric acid, phosphoric acid, alkanoic acids, alkylsulfonic acids, aromatic sulfonic acids, isethionic acid, and the like.

The compounds of the present invention may also form salts with a variety of organic and inorganic bases. Exemplary basic salts include ammonium salts, alkali metal salts such as lithium, sodium, potassium salts, alkaline earth metal salts such as calcium and magnesium salts, salts with organic bases (for example, organic amines) and salts with amino acids such as arginine, lysine and the like.

All stereoisomers of the present compounds (for example, those which may exist due to asymmetric carbons on various substituents), include enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The individual optical isomers can be obtained from the racemates by any suitable method, including without limitation, conventional methods, such as, for example, salt formation with an optically active acid or base followed by crystallization, or biocatalytic methods, for example, selective hydrolysis with a lipase.

DESCRIPTION OF THE INVENTION

The present invention relates to N-(3-substituted propyl)-2-aminobutyronitrile having formula (II),

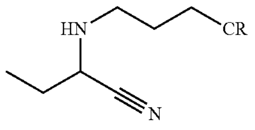

(II)

its preparation, and its use in preparing levetiracetam, wherein CR is a substituent selected from the group consisting of cyano, carboxylic acid, carboxamide, alkali carboxylate, alkaline earth metal carboxylate, alkyl carboxylate, and a mixture thereof.

The compound of formula (II) can be prepared economically and efficiently in a process comprised of reacting propionaldehyde, a source of cyanide, and a primary amine of formula $H_2NCH_2CH_2CH_2CR$, in a reaction as described in the following scheme:

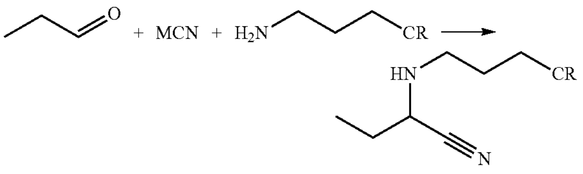

(II)

wherein CR is cyano, carboxylic acid, carboxamide, alkali carboxylate, alkaline earth metal carboxylate, alkyl carboxylate, and a mixture thereof, and wherein MCN represents the source of cyanide such as alkali cyanide, alkaline earth metal cyanide, zinc cyanide, or hydrogen cyanide.

A particularly useful primary amine is gamma-aminobutyric acid or its derivative. The neutral gamma-aminobutyric acid, which is available commercially and economically, may be preferably used. The addition salts of gamma-aminobutyric acid with a variety of acids may also be used. In addition, basic salts of gamma-aminobutyric acid can be used in the reaction. Preferably, alkali or alkaline earth metal gamma-aminobutyrate is prepared in situ by hydrolysis of 2-pyrrolidinone with an alkali hydroxide, or an alkaline earth metal oxide, or an alkaline earth metal hydroxide, or their mixture. The basic agent for the hydrolysis of 2-pyrrolidinone is selected from the group consisting of lithium hydroxide, sodium hydroxide, potassium hydroxide, magnesium oxide, magnesium hydroxide, calcium oxide, calcium hydroxide, barium oxide, barium hydroxide, and a mixture of two or more thereof.

The reaction to prepare the compound of formula (II) is carried out in an aqueous solution and optionally in the presence of an organic solvent. A suitable solvent is water-soluble and is selected from the group consisting of methanol, ethanol, propanol, isopropanol, butanol, isobutanol, tert-butanol, tetrahydrofuran, dioxane, methoxyethanol, ethoxyethanol, and a mixture thereof.

The method of preparing the compound of formula (II) according to the present invention also comprises reacting the Schiff base of the following formula:

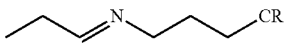

with a source of cyanide, wherein the Schiff base may be prepared in situ, comprising reacting propionaldehyde with a primary amine of the formula $H_2NCH_2CH_2CH_2CR$, wherein CR is cyano, carboxylic acid, carboxamide, alkali carboxylate, alkaline earth metal carboxylate, alkyl carboxylate, and a mixture thereof.

The method of preparing the compound of formula (II) according to the present invention further comprises reacting the cyanohydrin of propionaldehyde of the following formula:

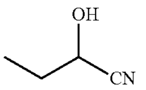

with a primary amine of the formula $H_2NCH_2CH_2CH_2CR$, wherein CR is cyano, carboxylic acid, carboxamide, alkali carboxylate, alkaline earth metal carboxylate, alkyl carboxylate, and a mixture thereof. The cyanohydrin of propionaldehyde can be prepared from the reaction of propionaldehyde and a source of cyanide such as such as alkali cyanide, alkaline earth metal cyanide, zinc cyanide, or hydrogen cyanide. The cyanohydrin can be prepared in situ and used as such or isolated as a pure product and then used.

After its preparation, the compound of formula (II) may be isolated from the reaction mixture. On the other hand, it may also be used as such to prepare levetiracetam according to various methods disclosed herein. The methods for preparing levetiracetam are illustrated in the following reaction schemes. Solvents, temperature, pressures, and other reaction conditions may readily be selected by one of ordinary skill in the art. Starting materials are commercially available or readily prepared by one of ordinary skill in the art.

In the first embodiment of the present invention to prepare levetiracetam, the compound of formula (II) is converted to (RS)-α-ethyl-2-oxo-1-pyrrolidineacetic acid of formula (IV) in a process comprising the steps according to the following reaction scheme:

Reaction Scheme 1

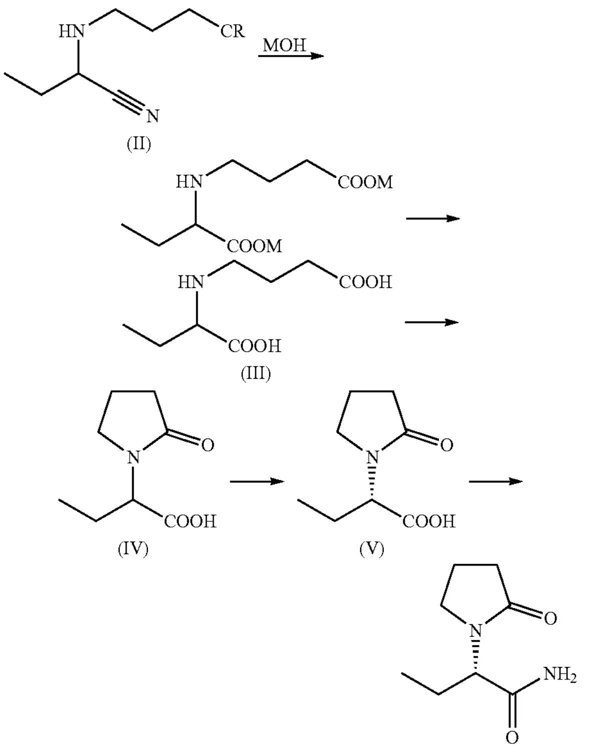

(II) (III) (IV) (V) (I)

wherein M is an alkali or an alkaline earth metal or their mixture. The alkali is lithium, sodium, potassium, or a mixture. The alkaline earth metal is magnesium, calcium, barium, or a mixture.

In this aspect of the first embodiment of the present invention, the cyano group in the compound of formula (II) is first hydrolyzed to the carboxylate by using an alkali hydroxide or an alkaline earth metal hydroxide or an alkaline earth metal oxide. A suitable hydroxide is selected from the group consisting of lithium hydroxide, sodium hydroxide, potassium hydroxide, cesium hydroxide, magnesium hydroxide, calcium hydroxide, barium hydroxide, magnesium oxide, calcium oxide, barium oxide, and a mixture of two or more thereof. The resulting carboxylate salt is acidified to form 2-N-(3-carboxypropyl)-aminobutyric acid of formula (III) by adding an acid. A suitable acid is selected from the group consisting of hydrochloric acid, sulfuric acid, nitric acid, phosphoric acid, hydrobromic acid, lower alkanoic acid, alkylsulfonic acid, aromatic sulfonic acid, and a mixture thereof.

It has now been found that the intermediate of formula (III) can be cyclized to form (RS)-α-ethyl-2-oxo-1-pyrrolidineacetic acid of formula (IV), the key intermediate and a well-known precursor to levetiracetam, under various reaction conditions.

In one method to prepare the key intermediate of formula (IV), the intermediate of formula (III) is heated to melt while removing the water formed during the cyclization. After no more water is released, the cyclization is complete. The product can be recrystallized from water or used for the next step of the process.

In another method to prepare the key intermediate of formula (IV), the intermediate of formula (III) is suspended in a solvent of a boiling point of at least 100° C. and heated to reflux to perform the cyclization reaction while removing the formed water. A suitable solvent is selected from the group consisting of toluene, xylenes, trimethylbenzene, cumene, cymene, dimethylformamide, dimethylacetamide, N-methylpyrrolidinone, dimethylsulfoxide, $C_4$-$C_{10}$ alcohols, and $C_2$-$C_8$ alkanoic acids.

In a further method to prepare the key intermediate of formula (IV), the intermediate of formula (III) is suspended in water and is heated to a temperature from 100° C. to 200° C. under autogenous pressure to perform the cyclization reaction from (III) to (IV). Preferably, the reaction temperature is from 110° C. to 180° C. More preferably, from 120° C. to 160° C. And most preferably, from 130° C. to 150° C. After the reaction, the product precipitates from the aqueous solution upon cooling. After separation of the product of formula (IV) by a solid-liquid separation, the mother liquor can be used to suspend a new batch of the intermediate (III) and to perform the cyclization reaction. This cyclic process of cyclization of the intermediate (III) results in a quantitative yield of the key intermediate (IV) without using any additional reagent.

It is particularly advantageous to carry out all steps of reactions leading to the key intermediate of formula (IV) in a one-pot synthesis, without the tedious isolation of any intermediate. This one-pot process of multiple reactions according to the present invention results in a concise process for preparing levetiracetam from basic starting materials such as 2-pyrrolidinone, a source of cyanide, and propionaldehyde. In this embodiment of the instant invention, 2-pyrrolidinone is hydrolyzed to an alkali or an alkaline earth metal gamma-aminobutyrate by using an alkali hydroxide, an alkaline earth metal hydroxide, or an alkaline earth metal oxide. To the solution of the alkali or alkaline earth metal gamma-aminobutyrate is added a source of cyanide, i.e., alkali cyanide, followed by the addition of propionaldehyde. Preferably, after 2-pyrrolidinone is hydrolyzed to an alkali gamma-aminobutyrate, the strongly alkaline solution is neutralized with an acid before the addition of alkali cyanide and propionaldehyde. After the formation of the intermediate of formula (II) is complete, to the solution is then added alkali hydroxide to hydrolyze the cyano group. The alkaline solution is then acidified with an acid to yield the key intermediate of formula (IV). A suitable acid is selected from the group consisting of hydrochloric acid, sulfuric acid, nitric acid, phosphoric acid, hydrobromic acid, lower alkanoic acid, alkylsulfonic acid, aromatic sulfonic acid, and a mixture thereof. The overall molar yield of the key intermediate of formula (IV) in this one-pot process is at least 50%, particularly more than 70%, more particularly more than 80%, most particularly more than 85%.

The racemic compound of formula (IV) is then optically resolved by using an optically active resolving agent. A suitable resolving agent can be selected from those listed in David Kozma, *CRC Handbook of Optical Resolution via Diastereomeric Salt Formation,* 2002, CRC Press, which is incorporated herein in its entirety. After optical resolution of the S-enantiomer, the R-enantiomer is racemized to the racemic form and subjected to optical resolution again. This cyclic resolution and racemization yield S-enantiomer in a yield of more than 50%, particularly more than 75% to nearly quantitative.

The optically pure S-enantiomer of formula (V) can be readily converted to levetiracetam of formula (I) by methods known in the prior art.

In the other aspect of the first embodiment of the present invention, the key intermediate of formula (IV) is prepared directly by reacting the compound of formula (II) with an acid to hydrolyze the nitrile group and to form the key intermediate of formula (IV) in situ in a process comprising the steps according to Reaction Scheme 2:

Reaction Scheme 2

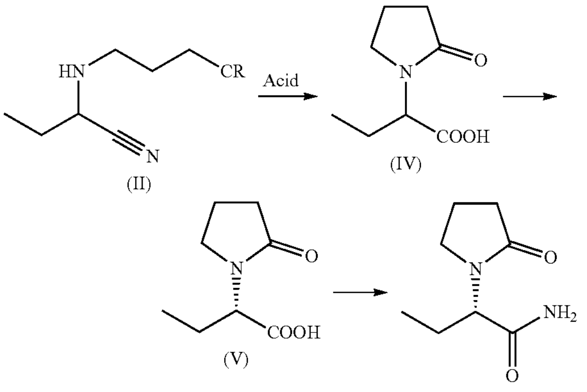

(II) (IV) (V) (I)

wherein CR is cyano, carboxylic acid, carboxamide, alkali carboxylate, alkaline earth metal carboxylate, alkyl carboxylate, and a mixture thereof.

A suitable acid is selected from the group consisting of sulfuric acid, hydrochloric acid, nitric acid, phosphoric acid, hydrobromic acid, alkylsulfonic acid, aromatic sulfonic acid, and a mixture of two or more thereof. Preferably, sulfuric acid is used to transform the compound of formula (II) to the intermediate of formula (IV).

In this embodiment of the instant invention, 2-pyrrolidinone is hydrolyzed to an alkali or alkaline earth metal gamma-aminobutyrate. To the solution of alkali or alkaline earth metal gamma-aminobutyrate is added a source of cyanide, i.e., alkali cyanide, followed by the addition of propionaldehyde. After the formation of the intermediate of formula (II) is complete, to the solution is then added an acid to hydrolyze the nitrile group and to cyclize the aminobutyric acid group to yield the key intermediate of formula (IV). A suitable acid is selected from the group consisting of sulfuric acid, hydrochloric acid, nitric acid, phosphoric acid, hydrobromic acid, alkylsulfonic acid, aromatic sulfonic acid, and a mixture of two or more thereof. The overall yield of the key intermediate of formula (IV) in this one-pot process is at least 50%, particularly more than 70%, more particularly more than 80%, most particularly more than 85%.

The one-pot process to prepare the intermediate of formula (IV) according to the present invention results in a concise process for preparing levetiracetam from basic starting materials such as 2-pyrrolidinone, a source of cyanide, and propionaldehyde.

In the second embodiment of the present invention to prepare levetiracetam, the compound of formula (II) is converted to the key intermediate of formula (IV) according to methods described in the first embodiment of the present invention and then to an ester of formula (VI) by reacting the compound of formula (IV) with an alcohol of the formula R'OH, wherein $R^1$ is a $C_1$-$C_{12}$ alkyl group, preferably, $C_1$-$C_4$ alkyl group. This racemic ester of formula (VI) is optically resolved by using a lipase to selectively hydrolyze the ester to an optically active ester (VII) and an optically active acid, which is used to prepare levetiracetam in a process comprising the steps according to the following reaction scheme:

Reaction Scheme 3.1

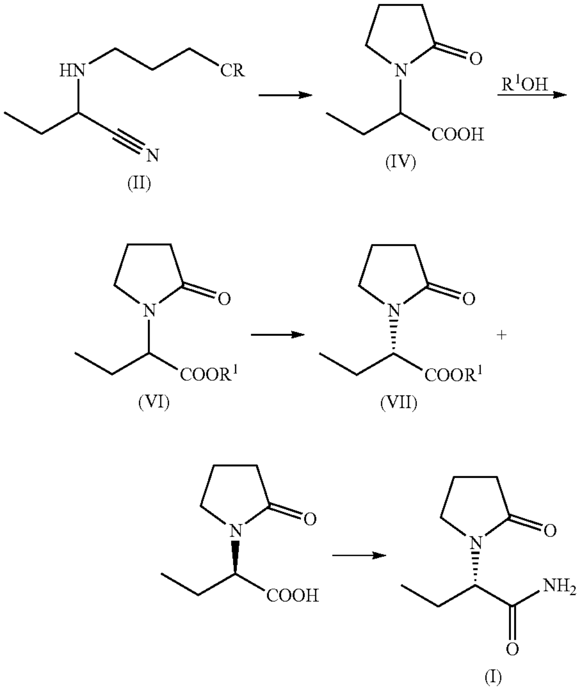

(II) (IV) (VI) (VII) (I)

wherein CR is cyano, carboxylic acid, carboxamide, alkali carboxylate, alkaline earth metal carboxylate, alkyl carboxylate, and a mixture thereof; and $R^1$ is a $C_1$-$C_{12}$ alkyl group, preferably, $C_1$-$C_4$ alkyl group. Suitable lipase has been disclosed in CN109943618A, which is incorporated herein by reference. The unwanted acid is then racemized and recycled.

In the other variant of the embodiment, the racemic ester of formula (VI) is optically resolved by using a lipase to selectively hydrolyze the ester to an optically active acid of formula (V), which is used to prepare levetiracetam in a process comprising the steps according to the following reaction scheme:

Reaction Scheme 3.2

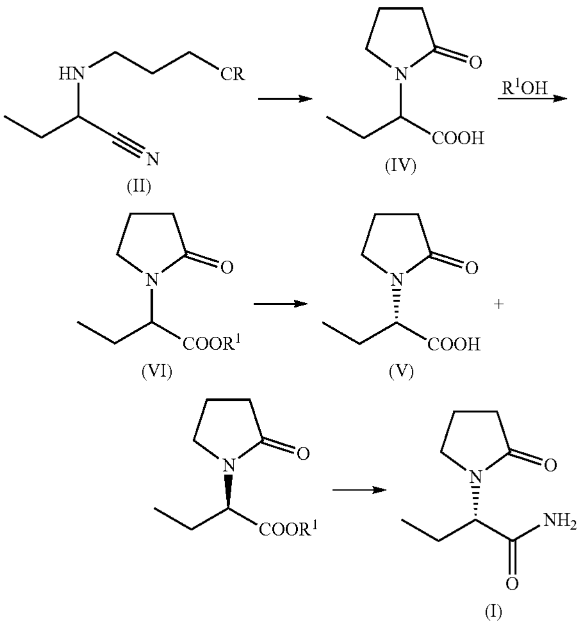

(II) (IV) (VI) (V) (I)

wherein CR is cyano, carboxylic acid, carboxamide, alkali carboxylate, alkaline earth metal carboxylate, alkyl carboxylate, and a mixture thereof; and $R^1$ is a $C_1$-$C_{12}$ alkyl group, preferably, $C_1$-$C_4$ alkyl group. Suitable lipase has been disclosed in WO2019/028671A1, which is incorporated herein by reference. The unwanted ester is then racemized and recycled.

In the third embodiment of the present invention, the compound of formula (II) is first converted to a diester of formula (VIII), which is then cyclized to the ester of formula (VI). The ester is then selectively hydrolyzed by a lipase to an optically active ester and an acid. Levetiracetam is prepared from the ester or acid according to Reaction Scheme 3.1 or 3.2.

Reaction Scheme 4

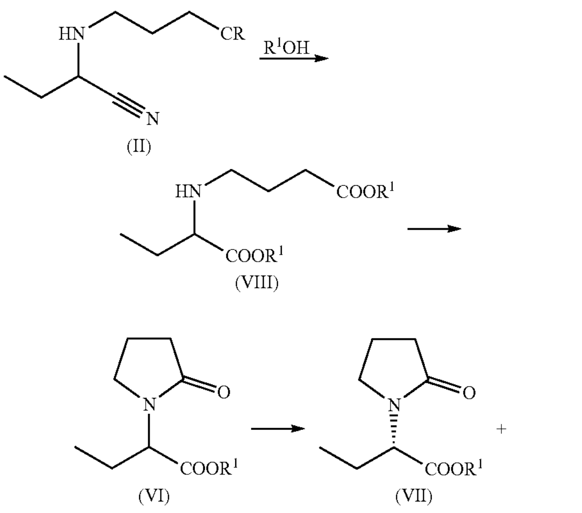

(II) (VIII) (VI) (VII)

-continued

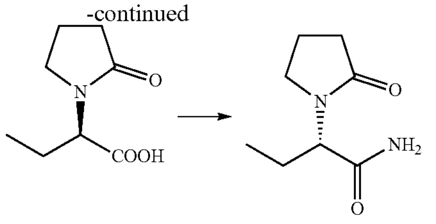

(I)

wherein CR is cyano, carboxylic acid, carboxamide, alkali carboxylate, alkaline earth metal carboxylate, alkyl carboxylate, and a mixture thereof; and $R^1$ is a $C_1$-$C_{12}$ alkyl group, preferably, $C_1$-$C_4$ alkyl group.

The formation of the diester of formula (VIII) is performed by reacting the compound of formula (II) with an alcohol $R^1OH$ in the presence of an acid, wherein $R^1$ is a $C_1$-$C_{12}$ alkyl group, preferably, $C_1$-$C_4$ alkyl group. A suitable acid is selected from the group consisting of hydrochloric acid, hydrobromic acid, sulfuric acid, nitric acid, alkylsulfonic acid, and arylsulfonic acid. Preferably, sulfuric acid is used. The formed diester may be isolated or used directly for the cyclization to form the compound of formula (VI). The cyclization reaction is carried out with a base and optionally in the presence of a phase transfer catalyst. A suitable base is selected from the group consisting of alkali hydroxide, alkali carbonate, alkali phosphate, alkali sulfite, alkaline earth metal hydroxide, alkaline earth metal oxide, or a mixture thereof. A suitable phase transfer catalyst is selected from the group consisting of quaternary ammonium salts and quaternary phosphonium salts. Preferably, benzyltriethylammonium chloride or tetrabutylammonium bromide is used.

In the fourth embodiment of the present invention, the compound of formula (II), wherein CR is an alkyl carboxylate, i.e., $COOR^1$, is cyclized to an intermediate of formula (IX):

Reaction Scheme 5

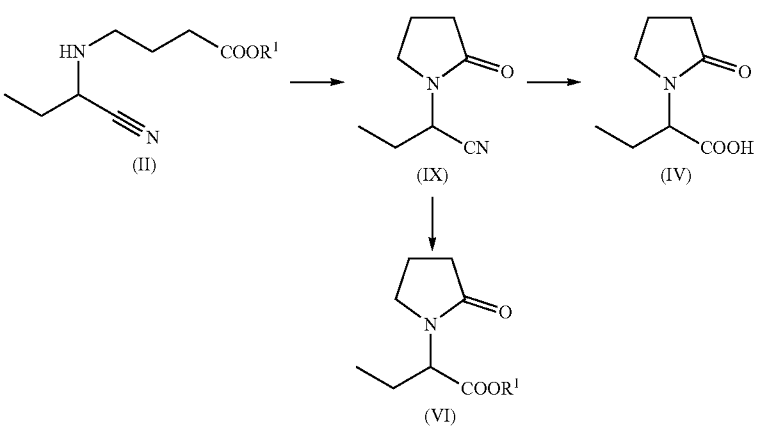

(II) (IX) (IV) (VI)

wherein $R^1$ is a $C_1$-$C_{12}$ alkyl group. Preferably, le is a $C_1$-$C_4$ alkyl group.

The formation of the compound of formula (IX) is performed with a base and optionally in the presence of a phase transfer catalyst. A suitable base is selected from the group consisting of alkali hydroxide, alkali carbonate, alkali phosphate, alkali sulfite, alkaline earth metal hydroxide, alkaline earth metal oxide, or a mixture thereof. A suitable phase transfer catalyst is selected from the group consisting of quaternary ammonium salts and quaternary phosphonium salts. Preferably, benzyltriethylammonium chloride or tetrabutylammonium bromide is used.

The nitrile group in the compound of (IX) can be hydrolyzed to a carboxylic acid to obtain the intermediate of formula (IV) or an ester to form the intermediate of formula (VI). These two intermediates are then optically resolved and converted to levetiracetam according to methods described in the first and second embodiments of the present invention.

EXAMPLES

The following examples will illustrate the practice of this invention but are not intended to limit its scope.

Example 1

To a solution comprised of 300 mL of water, 50 g of sodium cyanide, and 105 g of gamma butyric acid in a 1 L flask was dropwise added 58.0 g of propionaldehyde while maintaining the temperature below 25° C. After being stirred for 2 hours at room temperature, the solution was found to be comprised of 2-N-(sodium carboxylpropyl)-aminobutyonitrile of formula (II) in a molar yield of about 95%. LC-MS+1: 171. The solution was used without further purification.

Example 2

To a solution comprised of 300 mL of water, 50 g of sodium cyanide, and 105 g of gamma butyric acid in a 1 L flask was dropwise added 58.0 g of propionaldehyde while maintaining the temperature below 25° C. After the solution was stirred for 2 hours at room temperature, 60 g of sodium hydroxide was added and the solution was heated to reflux for 2 hours. Then, sulfuric acid was added to a pH of 3-4. After cooling to room temperature, the precipitated solid material was filtered and washed with ice water to yield 125 g of 2-N-(carboxypropyl)aminobutyric acid of formula (III). MS+1: 190.

Example 3

40.0 g of 2-N-(carboxylpropyl) aminobutyric acid was suspended in 200 mL of water containing 5 g of sulfuric acid in a glass pressure bottle. The suspension was heated to obtain a clear solution to 150° C. and maintained at the same temperature for 4 hours. After cooling to room temperature, crystalline solid was formed and filtered to yield 31 g of (RS)-α-ethyl-2-oxo-1-pyrrolidineacetic acid of formula (IV) as a white material. M.P. 154-156. MS+1: 172.

Example 4

To a solution comprised of 300 mL of water, 50 g of sodium cyanide, and 105 g of gamma butyric acid in a 1 L flask was dropwise added 58.0 g of propionaldehyde while maintaining the temperature below 25° C. The solution was stirred for 2 hours at room temperature before 150 g of sulfuric acid was added to the solution. The solution was placed in a pressure glass bottle and stirred in the bath at a temperature of 140-145° C. for 1 hours. Upon stopping the stirring, an oil phase was observed to separate. Further cooling to room temperature resulted in the formation of beige crystalline solid. Recrystallization from water with a small amount of decoloring charcoal yielded (RS)-α-ethyl-2-oxo-1-pyrrolidineacetic acid of formula (IV) as a white crystalline solid M.P. 154-156. MS+1: 172.

Example 5

To a solution comprised of 300 mL of water, 50 g of sodium cyanide, and 105 g of gamma butyric acid in a 1 L flask was dropwise added 58.0 g of propionaldehyde while maintaining the temperature below 25° C. After the solution was stirred for 2 hours at room temperature, 60 g of sodium hydroxide was added and the solution was heated to reflux for 2 hours. Then, sulfuric acid was added to a pH of 2.0. 140 g of sulfuric acid was used. The solution was then heated to 150° C. for 4 hours in an autoclave under autogenous pressure. After cooling to room temperature, the precipitated solid material was filtrated and washed with water. The off-white material was dissolved in hot water and decolorized with a little activated carbon to yield (RS)-α-ethyl-2-oxo-1-pyrrolidineacetic acid of formula (IV) as a white crystalline solid. M.P. 154-156° C. MS+1: 172.

Example 6

To a solution comprised of 60 g of sodium hydroxide and 250 mL of water was added 90 g of 2-pyrrolidinone. After the solution was refluxed for 2 hours, 50 g of sodium cyanide was added, followed by a dropwise addition of 58 g of propionaldehyde, while maintaining the temperature below 25° C. To the solution was then added 40 g of sodium hydroxide and the solution was refluxed for 2 hours. Then, sulfuric acid was added to a pH of 2.0. 160 g of sulfuric acid was used. The solution was then heated to 150° C. for 4 hours in an autoclave under autogenous pressure. After cooling to room temperature, the precipitated solid material was filtrated and washed with water. The off-white material was dissolved in hot water and decolorized with a little activated carbon to yield (RS)-α-ethyl-2-oxo-1-pyrrolidineacetic acid of formula (IV) as a white crystalline solid. M.P. 154-156° C. MS+1: 172.

Example 7

To 500 mL of toluene was added 170 g of white recrystallized (RS)-α-ethyl-2-oxo-1-pyrrolidineacetic acid of formula (IV) and 121 g of R-(+)-α-phenylethylamine. The solution was briefly heated to 90° C. Upon cooling to room temperature, crystalline salt formed, which was filtered. This salt was purified by heating to dissolve in 350 mL of toluene. The solution was cooled and filtered to obtain the R-(+)-α-phenylethylamine salt of (S)-α-ethyl-2-oxo-1-pyrrolidineacetic acid of formula (V).

The salt was dissociated in 300 mL of deionized water containing 12 g of sodium hydroxide. After the R-(+)-α-phenylethylamine was removed by extraction with toluene two times, the aqueous solution was acidified to pH 2-3 with sulfuric acid. The mixture was cooled on ice and the crystals were filtered off to obtain (S)-α-ethyl-2-oxo-1-pyrrolidineacetic acid of formula (V). M.P. 124-126° C.

40 g of the (S)-α-ethyl-2-oxo-1-pyrrolidineacetic acid of formula (V) was dissolved in 200 mL of anhydrous methanol containing 0.1 g of p-toluenesulfonic acid. After the solution was refluxing 2 hours to form the methyl ester, the solution was cooled on ice and ammonia was passed to the solution. The solution was kept at room temperature for 16 hours. After the excess ammonia and methanol were removed under vacuum, the residual solid was recrystallized in ethyl acetate to obtain 32 g of (S)-α-ethyl-2-oxo-1-pyrrolidineacetamide of formula (I). M.P. 117-118° C.

It will be understood that the foregoing examples, explanation, and drawings are for illustrative purposes only and that in view of the instant disclosure various modifications of the present invention will be self-evident to those skilled in the art. Such modifications are to be included within the spirit and purview of this application and the scope of the appended claims.

What is claimed is:

1. A process for producing (S)-α-ethyl-2-oxo-1-pyrrolidineacetamide of formula (I),

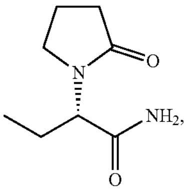

(I)

comprising:

(a) converting a compound of formula (II)

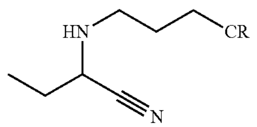

(II)

to (RS)-α-ethyl-2-oxo-1-pyrrolidineacetic acid of formula (IV):

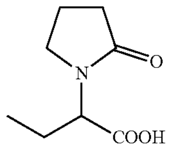

(IV)

wherein CR is selected from the group consisting of cyano, carboxylic acid, carboxamide, alkali carboxylate, alkaline earth metal carboxylate, alkyl carboxylate, and a mixture thereof; the alkali is lithium, sodium, potassium, or a mixture thereof; the alkaline earth metal is magnesium, calcium, barium, or a mixture thereof; and the alkyl is $C_1$-$C_{12}$;

(b) resolving the (RS)-α-ethyl-2-oxo-1-pyrrolidineacetic acid of step (a) into optically active (S)-α-ethyl-2-oxo-1-pyrrolidineacetic acid of formula (V):

(V)

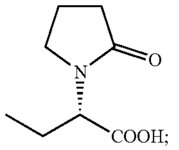

and (c) subjecting the (S)-α-ethyl-2-oxo-1-pyrrolidineacetic acid of formula (V) of step (b) to an amidation reaction to form (S)-α-ethyl-2-oxo-1-pyrrolidineacetamide of formula (I).

2. A process for producing (S)-α-ethyl-2-oxo-1-pyrrolidineacetamide of formula (I), (I)

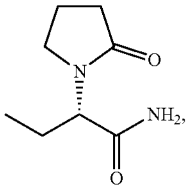

comprising:

(a) converting a compound of formula (II)

(II)

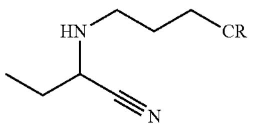

to (RS)-α-ethyl-2-oxo-1-pyrrolidineacetic acid ester of formula (VI):

(VI)

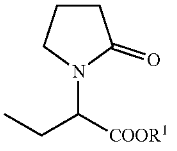

wherein CR is selected from the group consisting of cyano, carboxylic acid, carboxamide, alkali carboxylate, alkaline earth metal carboxylate, alkyl carboxylate, and a mixture thereof; the alkali is lithium, sodium, potassium, or a mixture thereof; the alkaline earth metal is magnesium, calcium, barium, or a mixture thereof; the alkyl is $C_1$-$C_{12}$; and $R^1$ is $C_1$-$C_{12}$;

(b) resolving the (RS)-α-ethyl-2-oxo-1-pyrrolidineacetic acid ester of step (a) to optically active (S)-α-ethyl-2-oxo-1-pyrrolidineacetic acid of formula (V):

(V)

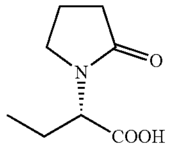

with a lipase; and (c) subjecting the (S)-α-ethyl-2-oxo-1-pyrrolidineacetic acid of formula (V) to an amidation reaction to form (S)-α-ethyl-2-oxo-1-pyrrolidineacetamide of formula (I).

3. A process for producing (S)-α-ethyl-2-oxo-1-pyrrolidineacetamide of formula (I), (I)

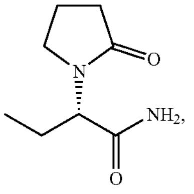

comprising:

(a) converting a compound of formula (II)

(II)

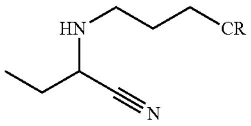

to (RS)-α-ethyl-2-oxo-1-pyrrolidineacetic acid ester of formula (VI):

(VI)

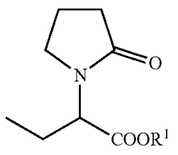

wherein CR is selected from the group consisting of cyano, carboxylic acid, carboxamide, alkali carboxylate, alkaline earth metal carboxylate, alkyl carboxylate, and a mixture thereof; the alkali is lithium, sodium, potassium, or a mixture thereof; the alkaline earth metal is magnesium, calcium, barium, or a mixture thereof; the alkyl is $C_1$-$C_{12}$; and $R^1$ is $C_1$-$C_{12}$;

(b) resolving the (RS)-α-ethyl-2-oxo-1-pyrrolidineacetic acid ester of step (a) into (S)-α-ethyl-2-oxo-1-pyrrolidineacetic acid ester of formula (VII):
(VII)
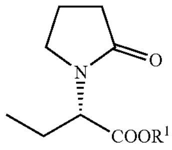
with a lipase; and
(c) subjecting the (S)-α-ethyl-2-oxo-1-pyrrolidineacetic acid ester of formula (VII) to an amidation reaction to form (S)-α-ethyl-2-oxo-1-pyrrolidineacetamide of formula (I).
* * * * *